(12) United States Patent
Shinmura et al.

US009102943B2

(10) Patent No.: US 9,102,943 B2
(45) Date of Patent: Aug. 11, 2015

(54) METHOD FOR PRODUCING VIRUS VECTOR

(75) Inventors: Kazuhisa Shinmura, Otsu (JP);
Yoshinori Katayama, Otsu (JP);
Kensuke Sakai, Otsu (JP); Toshihiro Shodai, Otsu (JP); Hirofumi Yoshioka, Otsu (JP); Junichi Mineno, Otsu (JP)

(73) Assignee: TAKARA BIO INC., Shiga (JP)

( * ) Notice: Subject to any disclaimer, the term of this patent is extended or adjusted under 35 U.S.C. 154(b) by 26 days.

(21) Appl. No.: 13/823,805

(22) PCT Filed: Oct. 4, 2011

(86) PCT No.: PCT/JP2011/072871
§ 371 (c)(1),
(2), (4) Date: Mar. 15, 2013

(87) PCT Pub. No.: WO2012/046727
PCT Pub. Date: Apr. 12, 2012

(65) Prior Publication Data
US 2013/0183719 A1    Jul. 18, 2013

(30) Foreign Application Priority Data
Oct. 5, 2010 (JP) ............................... 2010-225545

(51) Int. Cl.
| C12N 5/00 | (2006.01) |
|---|---|
| C12N 15/00 | (2006.01) |
| A61K 39/21 | (2006.01) |
| C12N 15/64 | (2006.01) |
| C12N 7/00 | (2006.01) |

(52) U.S. Cl.
CPC *C12N 15/64* (2013.01); *C12N 7/00* (2013.01); *C12N 2500/36* (2013.01); *C12N 2501/065* (2013.01); *C12N 2501/39* (2013.01); *C12N 2740/10051* (2013.01)

(58) Field of Classification Search
CPC ................. C12N 15/64; C12N 15/867; C12N 2501/065; C12N 2501/39
USPC .............. 435/325, 69.1; 424/207.1; 536/23.1, 536/23.72
See application file for complete search history.

(56) References Cited

U.S. PATENT DOCUMENTS

| 5,278,056 A | | 1/1994 | Bank et al. | |
|---|---|---|---|---|
| 5,470,726 A | * | 11/1995 | Miller et al. | .................. 435/465 |
| 6,787,359 B1 | | 9/2004 | Ueno et al. | |
| 7,485,448 B2 | | 2/2009 | Yoshioka et al. | |
| 2002/0183388 A1 | * | 12/2002 | Gudas et al. | .................. 514/559 |
| 2005/0064594 A1 | | 3/2005 | Gripon et al. | |
| 2005/0201983 A1 | | 9/2005 | Yla-Herttuala et al. | |
| 2008/0286239 A1 | * | 11/2008 | Nielsen et al. | ............... 424/93.2 |
| 2010/0113566 A1 | | 5/2010 | Chono et al. | |
| 2010/0137415 A1 | | 6/2010 | Chono et al. | |
| 2010/0273213 A1 | | 10/2010 | Mineno et al. | |

FOREIGN PATENT DOCUMENTS

| JP | 2004-535809 | 12/2004 |
|---|---|---|
| JP | 2007-105033 | 4/2007 |
| WO | 92/07943 | 5/1992 |
| WO | 00/01836 | 1/2000 |
| WO | 00/23567 | 4/2000 |
| WO | 01/96532 | 12/2001 |
| WO | 2007/020873 | 2/2007 |
| WO | 2008/133137 | 11/2008 |
| WO | 2009/048024 | 4/2009 |
| WO | 2009/143353 | 11/2009 |

OTHER PUBLICATIONS

Arts et al., Stimulation of tissue-type plasminogen activator gene expression by sodium butyrate and trichostatin A in human endothelial cells involves histone acetylation Biochem. J. (1995) 310,171-176.*
Gaetano et al Transcriptionally active drugs improve adenovirus vector performance in vitro and in vivo Gene Ther, 7 (2000), pp. 1624-1630.*
Soneoka et al., A transient three-plasmid expression system for the production of high titer retroviral vectors Nucl. Acids Res. (1995) 23 (4): 628-633.*
Hanai et al Endostatin Causes G1 Arrest of Endothelial Cells through Inhibition of Cyclin D1 JBC 1. 277, 16464-16469.*
Boyko et al., Coassembly and complementation of Gag proteins from HIV-1 and HIV-2, two distinct human pathogens. Molecular Cell 23, 281-287, Jul. 21, 2006.*
Eck et al., Goodman and Gilman's the Pharmacological Basis of Therapeutics, 1996 pp. 77-101.*
International Search Report issued Nov. 8, 2011 in International Application No. PCT/JP2011/072871.
Supplementary European Search Report issued Jun. 5, 2013 in corresponding European Patent Application No. 11830659.6.
International Preliminary Report on Patentability and Written Opinion issued May 8, 2013 in International Application No. PCT/JP2011/072871.
Jaalouk et al, "Inhibition of histone deacetylation in 293GPG packaging cell line improves the production of self-inactivating MLV-derived retroviral vectors", Virology Journal, Apr. 2006, vol. 3, No. 27, pp. 1-12.
Tobias et al., "Improved Recombinant Retroviral Titers Utilizing Trichostatin A", BioTechniques, Oct. 2000, vol. 29, No. 4, pp. 884-890.
Meier, Jeffery L., "Reactivation of the Human Cytomegalovirus Major Immediate-Early Regulatory Region and Viral Replication in Embryonal NTera2 Cells: Role of Trichostatin A, Retinoic Acid, and Deletion of the 21-Base-Pair Repeats and Modulator", Journal of Virology, Feb. 2001, vol. 75, No. 4, pp. 1581-1593.

(Continued)

*Primary Examiner* — Maria Leavitt
(74) *Attorney, Agent, or Firm* — Wenderoth, Lind & Ponack, L.L.P.

(57) ABSTRACT

The present invention provides a method for producing a virus vector, which comprises a step wherein cells that are capable of producing a virus vector are cultured in a culture medium that contains, as active components, a retinoic acid and a histone deacetylase inhibiting substance; and a culture medium for the production of a virus vector, which is characterized by containing, as active components, a retinoic acid and a histone deacetylase inhibiting substance.

7 Claims, 8 Drawing Sheets

(56) References Cited

OTHER PUBLICATIONS

Faluhelyi et al., "All-trans Retinoic Acid (ATRA) Suppresses Transcription of Human Papillomavirus Type 16 (HPV16) in a Dose-dependent Manner", Anticancer Research, 2004, vol. 24, pp. 807-810.

Kiefer et al., "Retinoic Acid Inhibition of Chromatin Remodeling at the Human Immunodeficiency Virus Type 1 Promoter", The Journal of Biological Chemistry, Oct. 2004, vol. 279, No. 42, pp. 43604-43613.

Nakashima, Hideki, "Inhibitory Effect of Retinoic Acid on Human Immuno-deficiency Virus (HIV) Infection and Replication in vitro", Vitamins (Japan), 1986, vol. 60, No. 11, pp. 527-535.

Caselli et al., "Retinoic acid analogues inhibit human herpesvirus 8 replication", Antiviral Therapy, 2008, vol. 13, pp. 199-209.

Olsen et al., "Use of Sodium Butyrate to Enhance Production of Retroviral Vectors Expressing CFTR cDNA", Human Gene Therapy, Sep. 1995, vol. 6, pp. 1195-1202.

Parente et al., "Production of increased titer retrovirus vectors from stable producer cell lines by superinfection and concentration", Gene Therapy, 1996, vol. 3, pp. 756-760.

Morgenstern et al., "Advanced mammalian gene transfer: high titre retroviral vectors with multiple drug selection markers and a complementary helper-free packaging cell line", Nucleic Acids Research, 1990, vol. 18, No. 12, pp. 3587-3596.

Danos et al., "Safe and efficient generation of recombinant retroviruses with amphotropic and ecotropic host ranges", Proc. Natl. Acad. Sci. USA, Sep. 1988, vol. 85, pp. 6460-6464.

Yasufumi Kaneda, "Vector Development for Cancer Gene Therapy", Biotherapy, vol. 20, No. 3, May 2006, pp. 261-269, with partial English translation.

Chinese Office Action issued Dec. 4, 2013 in corresponding Chinese Application No. 201180048256.4 (with English translation).

Office Action issued May 28, 2014 in corresponding Chinese Application No. 201180048256.4, with English translation.

Gang et al., "Enhancive Effect of Histone Deacetylase Inhibitor Trichostatin A on Transfection Efficiency of Adenovirus in Ovarian Carcinoma Cell Line A2780", Chinese Journal of Cancer, 2005, vol. 24, No. 10, pp. 1196-1200.

\* cited by examiner

METHOD FOR PRODUCING VIRUS VECTOR

TECHNICAL FIELD

The present invention relates to a method of producing a virus vector and a culture medium for production of a virus vector.

BACKGROUND ART

Gene therapy using a virus vector has been developed for the purposes of treating cancer and infection disease as well as congenital genetic disease, and many clinical trials have been conducted. In particular, many attempts for gene therapy using a retrovirus vector or an adenovirus vector have been made.

Examples of a transfer vector used for producing a recombinant retrovirus vector used for integration of a desired gene include pLXSN (Genbank Accession M28248) and pMFG which are derived from the wild-type Moloney murine leukemia virus (MoMLV) wherein viral particle-structural protein genes (gag, pol, env) are removed from the genome. In addition, a further modified vector is used in clinical trials for human.

A recombinant retrovirus vector is produced by transfecting a packaging cell (Psi-Crip, GP+E86, GP+envAm12, PG13, etc.) with a DNA vector in which a desired gene is inserted to induce a virus producer cell, culturing the virus producer cell, and then harvesting a supernatant containing the desired virus vector. Then, a packaging cell may be infected again with the supernatant, and from among the infected cells, a clone of a producer cell that can stably produce a retrovirus vector for expression of the desired gene may be selected. Through such a process, a master cell bank (MCB) and then a working cell bank are prepared, and therefrom a recombinant retrovirus vector for gene therapy is stably produced.

Culture of a retrovirus producer cell is very important for increasing the titer of a virus produced from the retrovirus producer cell. In other words, it is required to examine culture conditions for attaining higher viral titer. Methods of increasing viral titer so far as known involve multiple infection (for example, Non-Patent Literature 1), or addition of sodium butyrate or trichostatin A which is a histone deacetylase inhibitor (for example, Non-Patent Literatures 2 and 3). However, these known methods do not produce remarkable effects.

CITATION LIST

Non-Patent Literature

Non-Patent Literature 1: J. Hum. Gene Ther., Vol. 6, pp. 1195-1202 (1995)
Non-Patent Literature 2: Gene Therapy, Vol. 3, pp. 756-760 (1996)
Non-Patent Literature 3: BioTechniques, Vol. 29, pp. 884-890 (2000)

SUMMARY OF INVENTION

Technical Problems

Objectives of the present invention are to develop a culture medium used for production of a virus vector, in particular, a culture medium used for culture of a virus producer cell that can maintain higher viral titer, and provide a method of producing a virus vector which comprises using the culture medium and a method of producing a transformed cell population which comprises using the virus vector that is produced by the method of producing a virus vector.

Solution to Problems

The present inventors intensively studied to solve the above problems, and as a result, found that enhanced viral production could be continued for a long period and a virus supernatant having surprisingly high viral titer could be obtained when a virus producer cell was cultured using a culture medium containing retinoic acid and a histone deacetylase inhibitor as active ingredients. Thus the present invention was completed.

Specifically, the present invention relates to:
[1] A method of producing a virus vector, which comprises a step of culturing a cell capable of producing the virus vector in a culture medium containing retinoic acid and a histone deacetylase inhibitor as active ingredients;
[2] The method according to the above [1], wherein the culture medium further contains lipid as an active ingredient;
[3] The method according to the above [1] or [2], wherein the cell is a cell capable of producing the virus vector continuously;
[4] The method according to any one of the above [1] to [3], wherein the virus vector is a retrovirus vector;
[5] The method according to any one of the above [1] to [4], wherein the histone deacetylase inhibitor is at least one substance selected from the group consisting of trichostatin A and sodium butyrate;
[6] A virus vector produced by the method according to any one of the above [1] to [5];
[7] A method of producing a transformed cell population, which comprises transforming a cell with the virus vector according to the above [6];
[8] A transformed cell population obtained by the method according to the above [7];
[9] The cell population according to the above [8] for use in a medicament;
[10] The cell population according to the above [8] for use in production of a medicament;
[11] A pharmaceutical composition containing the cell population according to the above [8] as an active ingredient;
[12] A method of treating or preventing a disease, which comprises administering an effective amount of the pharmaceutical composition according to the above [11] to a subject; and
[13] A culture medium for production of a virus vector, containing retinoic acid and a histone deacetylase inhibitor as active ingredients.

Effects of Invention

According to the method of producing a virus vector of the present invention, viral production can be continued for a long period and high viral titer can be obtained, as compared with conventional methods. Therefore, according to the method of present invention, a large amount of a virus can be collected by one round of culture preparation. Furthermore, a virus vector prepared from a virus producer cell cultured in the culture medium of the present invention has a high viral titer, and therefore exhibits higher gene transduction efficiency than a virus vector obtained by a conventional method.

MODE FOR CARRYING OUT THE INVENTION

Figure 1:
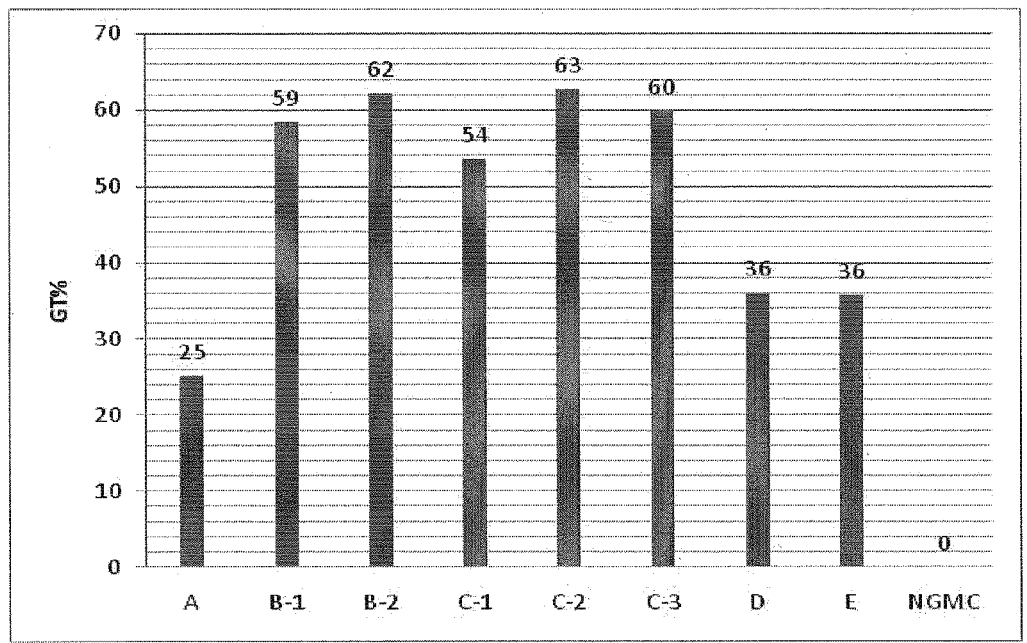
FIG. 1 shows gene transduction efficiency in SUP-T1 cells with retrovirus vectors obtained using culture media A, group B, group C, etc.

Hereinafter, the present invention is explained in detail.

The present invention discloses a culture medium suitable for culture of a cell producing a virus vector. The culture medium comprises a basal medium which is prepared by mixing necessary ingredients for cell culture and further contains retinoic acid and a histone deacetylase inhibitor as active ingredients. The culture medium may further contain lipid.

In the present invention, the "retinoic acid" is also called vitamin A acid, and may be either all-trans-retinoic acid, in which all double bonds on the chain part are in the trans form, or 9-cis-retinoic acid, in which a double bond at the 9-position is in the cis form. Other retinoic acid isomers, retinoic acid derivatives, and synthetic retinoids that are artificially synthesized can be also used in the present invention. As used herein, the above-described retinoic acids, retinoic acid isomers, retinoic acid derivatives, synthetic retinoids that are artificially synthesized, and their salts are collectively referred to as retinoic acid. The retinoic acid used in the present invention may be one kind of retinoic acid or a combination of plural kinds of retinoic acid.

The concentration of the retinoic acid used in the present invention in the culture medium is not particularly limited as long as it is such a concentration that the retinoic acid behaves as the active ingredient. When all-trans-retinoic acid (hereinafter, referred to as ATRA) is used, the concentration is, for example, preferably 1 nM to 10 µM, more preferably 5 nM to 200 nM, still more preferably 10 to 100 nM.

In the present invention, the "histone deacetylase inhibitor" may be any substance having histone deacetylase activity. Examples of the histone deacetylase inhibitor that can be used in the present invention include (1) fatty acids, such as butyric acid, phenyl butyric acid, valproic acid, and their salts, derivatives, and the like (2) hydroxamic acids, such as trichostatin A, oxamflatin, suberoylanilide, and their salts, derivatives, and the like, (3) cyclic peptides, such as trapoxin, apicidin, FK228, and their salts, derivatives, and the like, and (4) benzamide, and its salt, derivative, and the like.

Preferred examples of the histone deacetylase inhibitor include, but not limited to, sodium butyrate (hereinafter, referred to as NaB), and trichostatin A (hereinafter, referred to as TSA) which can inhibit a broad range of isoforms of histone deacetylases.

The concentration of the histone deacetylase inhibitor used in the present invention in the culture medium is not particularly limited as long as it is such a concentration that the histone deacetylase inhibitor behaves as the active ingredient. When TSA is used, the concentration is, for example, preferably 10 nM to 50 µM, more preferably 20 nM to 10 µM, still more preferably 100 nM to 3 µM. When NaB is used, the concentration is, for example, preferably 1 nM to 50 mM, more preferably 1 mM to 10 mM.

The culture medium containing retinoic acid and a histone deacetylase inhibitor of the present invention may further contain lipid. Examples of the lipid that can be used in the present invention include fatty acids (arachidonic acid, linoleic acid, linolenic acid, myristic acid, oleic acid, palmitoylic acid, palmitic acid, and their salts, and the like); steroids such as cholesterols, and dexamethasones; tocopherol acetate; triglycerides; and phospholipids (glycerophospholipid, sphingophospholipid, inositolphospholipid, and the like). One kind or a combination of plural kinds of the lipid as described above may be added to the culture medium. For example, the culture medium may contain a fatty acid concentrate as it is, which is commercially available as a medium additive to substitute for serum components.

The concentration in the culture medium of any lipid selected from the above-described lipids that can be used in the present invention is not particularly limited as long as it is such a concentration that the lipid behaves as the active ingredient. The total lipid concentration in the culture medium is preferably 0.01 mg/L to 8.0 mg/L, more preferably 0.03 mg/L to 5.0 mg/L, still more preferably 0.1 mg/L to 4.0 mg/L. For example, when the fatty acid concentrate is used, the concentration in terms of a volume ratio is preferably 1/10,000 to 1/50 (V/V), more preferably 1/3,000 to 1/75 (V/V), still more preferably 1/1,000 to 1/100 (V/V).

Examples of the ingredients of the basal medium include energy sources such as amino acids, saccharides and organic acids, vitamins, buffering ingredients for pH adjustment, and inorganic salts. The basal medium may also contain a pH indicator such as phenol red. Examples of the basal medium that may be used include known serum-free culture media, such as DMEM, IMDM, and Ham's F12 medium which are commercially available from Invitrogen, Sigma, and the like. Commercially available culture medium such as Opti-ProSF, VP-SFM, 293SFMII (which are manufactured by Invitrogen), and HyQ SFM4 MegaVir (manufactured by HyClone Laboratories Inc) can be also used. Although a serum-supplemented culture medium may be used, a serum-free culture medium is preferably used in order to prevent contamination with serum-derived unknown viruses. When a serum-free culture medium is used, a serum-free culture medium containing serum albumin highly purified from human blood (e.g., a serum albumin preparation approved as a drug), highly purified serum albumin derived from an animal, or recombinant serum albumin is preferably used (JP-A 2007-105033).

A virus producer cell to be cultured in the culture medium of the present invention is not particularly limited, and for example, preferred is a retrovirus producer cell.

The present invention relates to a method of producing a virus vector which comprises using the culture medium as described above.

The virus vector that can be produced according to the present invention is not particularly limited. Examples of the virus vector include retrovirus vectors (including oncovirus vectors, lentivirus vectors, and their modified forms), adenovirus vectors, adeno-associated virus vectors, simian virus vectors, vaccinia virus vectors, and sendaivirus vectors. Preferred examples of the virus vector include retrovirus vectors, namely, recombinant retrovirus vectors. Particularly, a retrovirus vector lacking the replication ability so as to prevent unlimited infection or gene transfer is preferably used in the present invention. Examples of known retrovirus vector lacking the replication ability include retrovirus vectors such as a MFG vector, an α-SGC vector (WO92/07943), pBabe [Nucleic Acids Research, vol. 18, No. 12, pp. 3587-3596 (1990)], LXIN (manufactured by Clontech), and DON-AI (manufactured by TAKARA BIO INC.), lentivirus vectors [human immunodeficiency virus (HIV)-derived vectors, simian immunodeficiency virus (SIV)-derived vectors, etc.], and vectors obtained by modifying them (e.g., pseudotyped vectors).

Into the virus vector as described above, any foreign gene may be introduced. The foreign gene to be introduced is not particularly limited, and any gene [a gene encoding protein such as an enzyme, a cytokine, or a receptor, as well as a gene encoding an intracellular antibody, an antisense nucleic acid, an siRNA (small interfering RNA), or ribozyme] can be used depending on the intended uses of a cell population transformed with the virus vector produced according to the present invention as described below. Examples of the foreign gene include, for the purpose of medical use of cells, a gene expressing MazF which is a sequence-specific ribonuclease (e.g., WO 2007/020873 and WO 2008/133137), a gene encoding an antibody variable region that recognizes a tumor antigen or a viral antigen, or a T cell receptor, and a gene which is lacked or whose function is lost in a patient. At the same time, a suitable marker gene that allows for selection of a gene-transduced cell, such as an extracellular domain gene of a low affinity nerve growth factor receptor (ΔLNGFR), a neomycin-resistant gene, or a fluorescent protein gene may be introduced into the virus vector.

For example, the foreign gene can be inserted into the virus vector in such a manner that the gene is expressed under the control of a suitable promoter. An enhancer sequence, a terminator sequence, or an intron sequence may be also present in the vector.

In the present invention, the production of the virus vector is carried out by transfecting a DNA encoding the virus vector into a packaging cell line to prepare a virus producer cell, and culturing the virus producer cell in the culture medium of the present invention.

The packaging cell line is not particularly limited, and a known packaging cell line, such as PG13 (ATCC CRL-10686), PA317 (ATCC CRL-9078), GP+E-86 or GP+envAm-12 (U.S. Pat. No. 5,278,056), or Psi-Crip [Proc. Natl. Acad. Sci. USA, vol. 85, pp. 6460-6464 (1988)] can be used. A packaging plasmid carrying genes necessary for production of retroviral particles (Retrovirus Packaging Kit manufactured by TAKARA BIO INC., etc.) can be also transfected into a 293 cell or a 293 T cell having a high transfected efficiency to prepare a retrovirus producer cell.

The method of the present invention can be applied to either a virus producer cell line prepared so as to transiently produce a recombinant virus vector, or a virus producer cell line capable of continuously producing a virus. In the case where the latter virus producer cell line is used, a frozen stock of the virus producer cell line such as a master cell bank (MCB) or a working cell bank (WCB) is thawed by a suitable means, and then directly seeded in the culture medium to start the culture, and the cell is grown to allow the cell to produce the virus. For preparation of a recombinant virus vector in large scale, it is preferable that an acclimation step for adapting the virus producer cell line to the culture medium is further added.

The virus producer cell can be cultured under conventional culture conditions. Examples of the culture conditions include, but not limited to, culture at 95% of humidity and 5% $CO_2$. The culture of the virus producer cell can be carried out, for example at 30 to 37° C. However, the culture of the virus producer cell may be carried out at a temperature falling outside the above-described range as long as it is such a temperature that the growth of the desired cell and the production of the virus vector can be attained. In the present invention, supernatant is harvested from the culture solution thus obtained, and a virus vector is obtained therefrom. In the present invention, the virus vector may be the above-described supernatant as it is, or a filtrate obtained by filtering the supernatant, or may be concentrated or purified by a known method. The virus vector is kept by a suitable means, for example by freezing, until use. According to the culture of the virus producer cell in the culture medium of the present invention as described above, a virus vector with higher titer can be obtained as compared with a conventional culture method.

The present invention also provides a method of producing a cell population containing transformed cells which comprises transforming a target cell with the virus vector produced by the method of the present invention. The number of the desired genes to be transduced into a cell by the virus vector is not limited. One gene or two or more genes may be transduced by the virus vector. The transduction of the target cell with the virus vector may be carried out by a known method suitable for the virus vector. For example, when a retrovirus vector is used, a substance capable of enhancing gene transduction efficiency such as RetroNectin (registered trademark; manufactured by TAKARA BIO INC.) can be also used at the time of carrying out gene transduction.

Since a virus vector with high viral titer can be obtained according to the present invention, a cell population comprising a high percentage of cells retaining a desired gene can be obtained by using the virus vector.

The present invention provides a cell population obtained by the method of producing a cell population of the present invention, and use of the cell population. The cell population obtained by the method of the present invention can be used for various purposes, for example for production of useful substances. The cell population itself can be also used for treatment of disease.

According to the method of the present invention, a cell population containing cells retaining a therapeutically useful foreign gene can be obtained. The cell population can be used for treatment of various diseases, such as cancer, leukemia, malignant tumors, hepatitis, infectious diseases [e.g., influenza, tuberculosis, HIV (Human Immunodeficiency virus) infectious disease, MRSA infectious disease, VRE infectious disease, and deep mycosis], and the like. The cell population produced by the method of the present invention can be also utilized in combination with a conventional therapeutic method, such as donor lymphocyte infusion for the purpose of prevention of infectious disease in an immunodeficiency state after bone marrow transplantation, exposure to radiation, or the like, or remission of relapsed leukemia, anticancer drug therapy, radiation therapy, antibody therapy, thermotherapy, or other immunotherapy.

When the cell population containing transformed cells obtained according to the present invention is used for treatment or prevention of disease, an effective amount of the cell is administered to a subject for the treatment or prevention, that is, a human or a non-human animal. A method of administration of the cell population may be selected appropriately depending on the disease. Examples of the administration method include intravenous administration, intraarterial administration, subcutaneous administration, and intraperitoneal administration, by injection or infusion.

The cell population obtained according to the present invention can be formulated into a pharmaceutical composition, that is, a therapeutic agent or a preventive agent for disease, and can treat or prevent the disease by administering the pharmaceutical composition to a subject. The pharmaceutical composition can be produced by formulating the cell population according to a method known in the pharmaceutical filed. For example, the cell population produced by the method of the present invention as the active ingredient can be mixed with a known organic or inorganic carrier, excipient or stabilizer which is suitable for parenteral administration, or the like to prepare an infusion or an injection.

EXAMPLES

Hereinafter, the present invention is further specifically explained by means of Examples to which the present invention is not limited.

Example 1

Preparation of Trichostatin A-supplemented Culture Medium

A serum-free culture medium for culture of virus producer cells, GT-T-Retrol (manufactured by TAKARA BIO INC., hereinafter, referred to as Retrol) was used as a basal medium A (culture medium A). To the culture medium A were added retinoic acid (ATRA) (manufactured by Wako Pure Chemical Industries, Ltd.) at final concentrations of 10 nM and 100 nM, and trichostatin A (TSA) (manufactured by Sigma) at a final concentration of 500 nM to prepare culture media B-1 and B-2 respectively (hereinafter, referred to as a culture medium group B). Furthermore, to the culture medium B-1 was added a fatty acid concentrate (manufactured by Gibco, hereinafter, referred to as lipid) at volume ratios (V/V) of 1/100, 1/250 and 1/1000 to prepare culture media C-1, C-2 and C-3 respectively (hereinafter, referred to as a culture medium group C). In addition, a culture medium D which was the culture medium A supplemented with only TSA (final concentration: 500 nM), and a culture medium E which was the culture medium A supplemented with only ATRA (final concentration: 10 nM) were prepared. The composition of each culture medium is shown in Table 1.

TABLE 1

| Culture medium | | ATRA | TSA | lipid (V/V) |
|---|---|---|---|---|
| A | | — | — | — |
| B-1 | Group B | 10 nM | 500 nM | — |
| B-2 | | 100 nM | 500 nM | — |
| C-1 | Group C | 10 nM | 500 nM | 1/100 |
| C-2 | | 10 nM | 500 nM | 1/250 |
| C-3 | | 10 nM | 500 nM | 1/1000 |
| D | | — | 500 nM | — |
| E | | 10 nM | — | — |

Example 2

1. Culture of Retrovirus Producer Cell

A working cell bank (WCB) of a retrovirus producer cell capable of producing a mouse-derived recombinant retrovirus vector carrying a fluorescent reporter protein (ZsGreen) gene (PG13: ATCC CRL-10686 was used as a packaging cell) was thawed in a water bath at 37° C. The cell solution thus thawed was put into a 15 mL centrifuging tube. After addition of 10 mL of a complete medium [a DMEM medium (manufactured by Gibco) containing 10% fetal bovine serum (10% FBS, manufactured by SAFC Biosciences)], the tube was subjected to centrifugation (500×g, 5 minutes, 20° C.). After the centrifugation, a supernatant was removed, and the cells were suspended in 10 mL of the complete medium and then counted. After cell counting, the cell suspension was adjusted with the complete medium to $78.5 \times 10^4$ cells/mL. To a 100 mm dish for cell culture (manufactured by IWAKI) were added 1 mL of the cell suspension and 14.7 mL of the complete medium. The cell culture was carried out in a $CO_2$ incubator (37° C., 95% of humidity, 5% $CO_2$). The cell was subcultured at intervals of 3 days. At the 1st passage, the cell suspension was seeded at the cell density of $1 \times 10^4$ cells/cm$^2$ and the volume of 0.2 mL/cm$^2$. At the 2nd passage, 2 mL/well of the cell suspension was seeded at the cell density of $0.9 \times 10^4$ cells/cm$^2$ and the volume of 0.2 mL/cm$^2$ onto a 6-well treated plate for cell culture (manufactured by BD Falcon). Three days after the start of culture at the 2nd passage, a culture supernatant was removed and replaced with the culture medium A, B-1, B-2, C-1, C-2, C-3, D or E as described in Example 1 (volume: 0.1 mL/cm$^2$). On the following day, the culture medium was collected and replaced with a fresh culture medium that was of the same kind as that of the collected culture medium. After lapse of 3 days at the 2nd passage, the cell culture was carried out at 32° C., 95% of humidity and 5% $CO_2$. The collection and replacement of the culture medium were carried out a total of 4 times for consecutive 4 days, provided that for the 4th time, only the collection of the culture medium was carried out and a fresh culture medium thereof was not added. Each of the collected culture supernatants (the 1st, 2nd, 3rd and 4th times) was filtered through a filter with pore size of 0.22 μm (manufactured by Millipore). The filtrate of each culture supernatant was aliquoted and then kept at −80° C. as a retrovirus supernatant for each time.

2. Evaluation of Gene Transduction with Retrovirus Supernatant

The gene transduction efficiencies of the retrovirus supernatants collected using the culture media A to E as described above were determined. Each of the retrovirus supernatants collected using the media A to E was diluted to prepare a 5-fold diluted solution. For the dilution of the retrovirus supernatants, ACD-A (manufactured by Terumo Corporation), and a 5-fold or 12.5-fold diluted solution of human serum albumin "Albuminar 25%" (manufactured by CSL Behring) which was prepared with addition of a physiological saline so as to have the final albumin concentration of 5% or 2% respectively (hereinafter, referred to as a 5% albumin solution or a 2% albumin solution) were used. As a vessel for gene transduction, a 24-well nontreated plate (manufactured by BD Falcon) was used. The 24-well nontreated plate was treated at 4° C. overnight with addition of 0.5 mL/well of a solution of RetroNectin (registered trademark, manufactured by TAKARA BIO INC.) which was previously diluted with ACD-A so as to have the final concentration of 20 µg/mL. After the solution of RetroNectin was removed from the plate, the plate was washed 2 times by addition of 0.5 mL of ACD-A to each well and then removal of the ACD-A. To each well of the washed plate was added 1 mL of each virus diluted solution. The plate was subjected to centrifugation (32° C., 2000× g, 2 hours). After centrifugation, a supernatant of the virus diluted solution was removed from each well. Each well was washed 3 times with 0.5 mL of a 16.67-fold diluted solution of human serum albumin "Albuminar 25%" which was prepared with addition of a physiological saline so as to have the final albumin concentration of 1.5% (hereinafter, referred to as a 1.5% albumin solution). A human T lymphocytic leukemic cell SUP-T1 (ATCC CRL-1942) was suspended at $1 \times 10^6$ cells/mL in a medium for culture of SUP-T1 cells [a RPMI1640 medium (manufactured by Sigma) containing 10% fetal bovine serum]. To each well of the washed 24-well nontreated plate as described above was added 1 mL of the SUP-T1 cell suspension ($0.5 \times 10^6$ cells/cm$^2$). The plate was subjected to centrifugation (32° C., 1000×g, 10 minutes). After centrifugation, the cell was cultured for 1 day in a CO$_2$ incubator (37° C., 95% of humidity, 5% CO$_2$). On the following day, 1 mL of the medium for culture of SUP-T1 cells was added to each well, and the cell was further cultured for 1 day. After the culture, the expression of the fluorescent reporter protein (ZsGreen) was checked to determine the gene transduction efficiency of the retrovirus. Then, $0.5 \times 10^6$ cells of the infected and cultured cell were put into an Eppendorf tube, and then precipitated by centrifugation (4° C., 500×g, 5 minutes). After a supernatant was removed, the precipitated cells were suspended in 950 µL of a phosphate buffer (manufactured by Gibco) supplemented with BSA (fetal bovine serum albumin, manufactured by Sigma) at the final concentration of 0.5% (hereinafter, referred to as 0.5% BSA/PBS). Then, the cells were precipitated again by centrifugation (4° C., 500×g, 5 minutes). After a supernatant was removed, the precipitated cells were suspended in 400 µL of 0.5% BSA/PBS which was a phosphate buffer (manufactured by Gibco) supplemented with 0.5% BSA (manufactured by Sigma). The cell suspension was subjected to flow cytometry measurement.

3. Flow Cytometry Analysis

Flow cytometry analyses were carried out using a BD FACSCanto II flow cytometer (Becton, Dickinson and Company) according to the instructions attached to the equipment. The expression rate of ZsGreen was determined as follows. On a 2-parameter histogram of a forward scattered light (FSC) and a side scattered light (SSC) (x-axis: FSC, y-axis: SSC), a cell population of interest was gated. The cell population within the gate was developed with a histogram of a GFP-detected parameter (x-axis: fluorescence intensity of GFP, y-axis: cell counts). A cell having a higher GFP fluorescence intensity than an isotype control was defined as a ZsGreen-positive cell. The rate (%) of the number of ZsGreen-positive cells relative to the total number of cells in the above-described gated cell population was defined as a gene transduction efficiency (GT %), and a mean fluorescence intensity (MFI) was measured.

Measurement results of gene transduction efficiency are shown in FIG. 1.

The virus supernatant obtained on each day by the culture method of Example 2-2 was evaluated for the gene transduction efficiency, and the average value of the virus supernatants obtained over 4 days was calculated. As shown in FIG. 1, the gene transduction efficiencies of the retrovirus supernatants collected using the culture medium groups B and C were at least 2 times higher than in the case of using the culture medium A which was a basal medium. In other words, when the culture medium groups B and C were used, viruses with higher titer were obtained and the ZsGreen gene was transduced with higher efficiency by the viruses as compared with the case of using the culture medium A. As compared with the case of using the culture medium D or E, the use of the culture medium groups B and C also produced the above-described effects greater than in the case where only TSA or ATRA was added.

In Figure, "NGMC" means a cell that has not been transduced with a gene, and represents a negative control. In FIGS. 2 to 15, "NGMC" has the same meaning.

Figure 2:
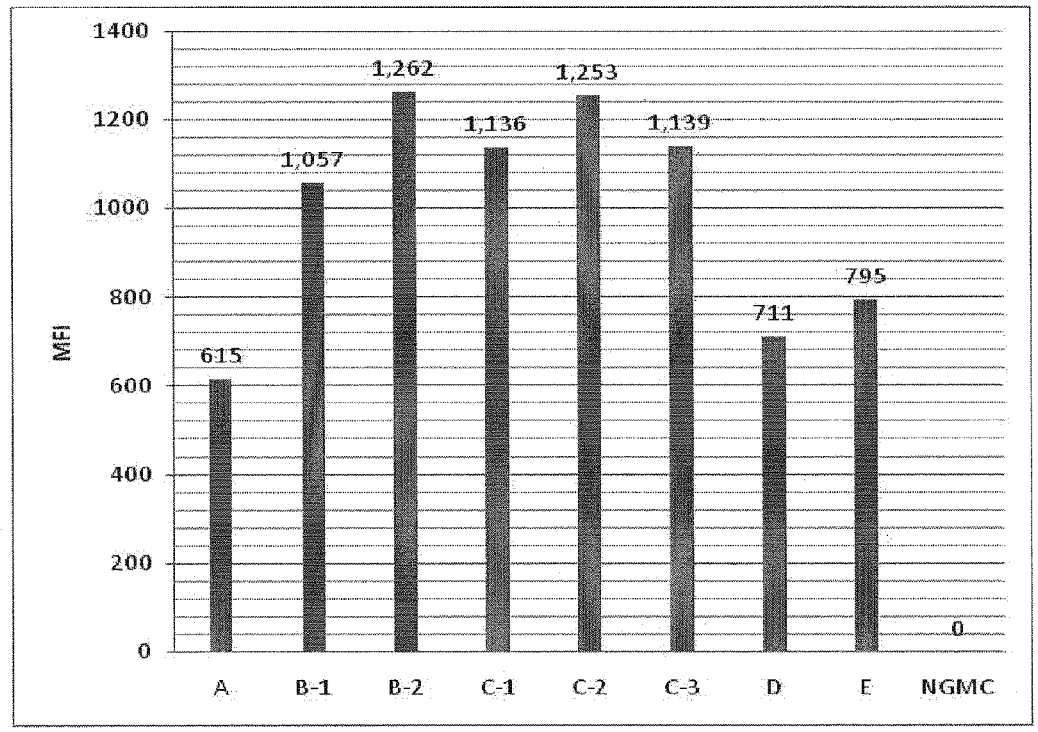
FIG. 2 shows expression intensity of a gene that has been transduced into SUP-T1 cells with retrovirus vectors obtained using culture media A, group B, and group C, etc.

Measurement results of fluorescence intensity (hereinafter, which means gene expression intensity) are shown in FIG. 2.

The virus supernatant obtained on each day by the culture method of Example 2-2 was evaluated for the fluorescence intensity, and the average value of the virus supernatants obtained over 4 days was calculated. As shown in FIG. 2, the fluorescence intensities of the retrovirus supernatants collected using the culture medium groups B and C were about 2 times higher than in the case of using the culture medium A. In other words, when the culture medium groups B and C were used, viruses with higher titer were obtained and the gene was transduced with higher efficiency by the viruses, thereby the fluorescent reporter protein (ZsGreen) was more highly expressed, as compared with the case of using the culture medium A. As compared with the case of using the culture medium D or E, the use of the culture medium groups B and C also produced the above-described effects greater than in the case where only TSA or ATRA was added.

Example 3

Preparation of NaB-supplemented Culture Medium

To the culture medium A as described in Example 1 were added ATRA at final concentrations of 10 nM and 100 nM, and sodium butyrate (NaB) at a final concentration of 5 mM to prepare culture media F-1 and F-2 respectively. Furthermore, to the culture medium F was added the lipid at volume ratios (V/V) of 1/100, 1/250 and 1/1000 to prepare culture media G-1, G-2 and G-3 respectively. In addition, a culture medium H which was the culture medium A supplemented with only NaB (final concentration: 5 mM), and a culture medium E which was the culture medium A supplemented with only ATRA (final concentration: 10 nM) were prepared. The composition of each culture medium is shown in Table 2.

TABLE 2

| Culture medium | | ATRA | NaB | lipid (V/V) |
|---|---|---|---|---|
| A | | — | — | — |
| F-1 | Group F | 10 nM | 5 mM | — |
| F-2 | | 100 nM | 5 mM | — |
| G-1 | Group G | 10 nM | 5 mM | 1/100 |

TABLE 2-continued

| Culture medium | ATRA | NaB | lipid (V/V) |
|---|---|---|---|
| G-2 | 10 nM | 5 mM | 1/250 |
| G-3 | 10 nM | 5 mM | 1/1000 |
| H | — | 5 mM | — |
| E | 10 nM | — | — |

Example 4

Culture of Retrovirus Producer Cell

The retrovirus producer cell as described in Example 2 was used to prepare virus supernatants. In this Example, the virus supernatants were obtained in the same manner as Example 2-1 except that the culture media A, group F, group G, H and E as described in Example 3 were used. Gene transduction was carried out in the same manner as Example 2-2. Evaluation of gene transduction efficiency was carried out in the same manner as Example 2-3.

Figure 3:
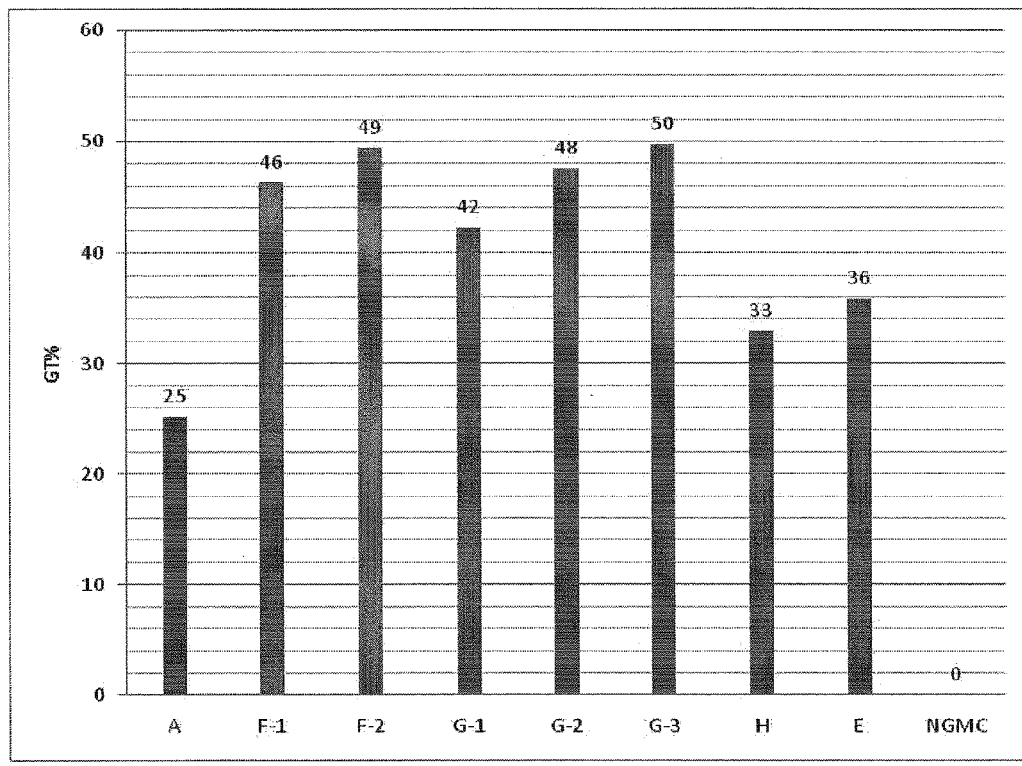
FIG. 3 shows gene transduction efficiency in SUP-T1 cells with retrovirus vectors obtained using culture media A, group F, group G, etc.

Measurement results of gene transduction efficiency are shown in FIG. 3.

As shown in FIG. 3, the gene transduction efficiencies of the retrovirus supernatants collected using the culture medium groups F and G were about 2 times higher than in the case of using the culture medium A. In other words, when the culture medium groups F and G were used, viruses with higher titer were obtained and the ZsGreen gene was transduced with higher efficiency by the viruses as compared with the case of using the culture medium A. The use of the culture medium groups F and G also produced higher effects as compared with the case of using the culture medium H or E (addition of only NaB or ATRA).

Figure 4:
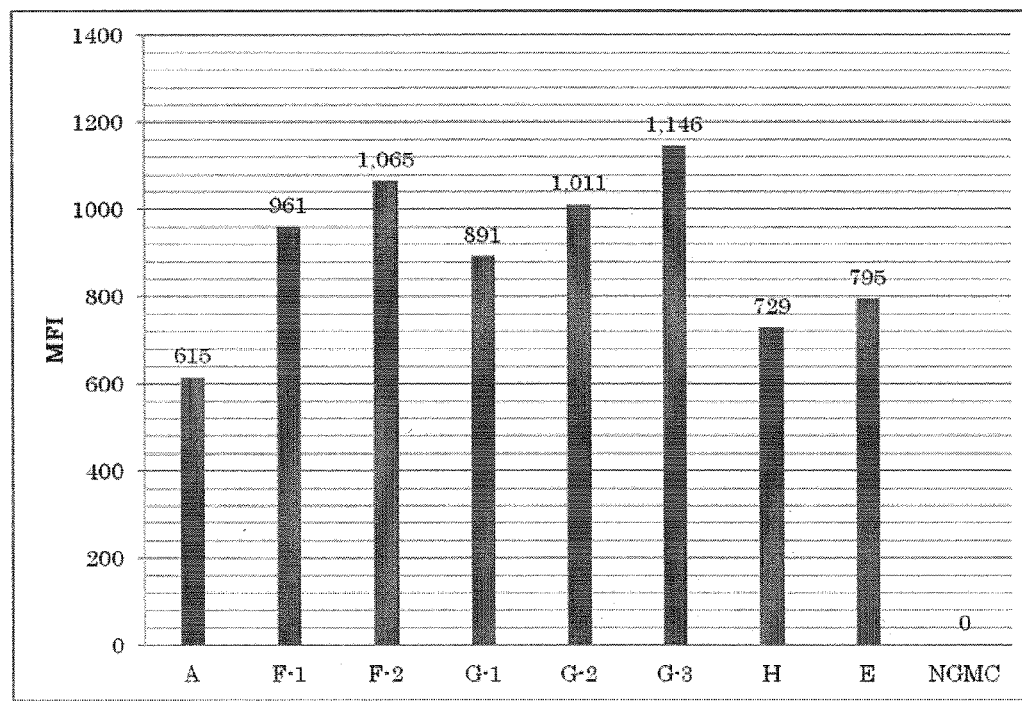
FIG. 4 shows expression intensity of a gene that has been transduced into SUP-T1 cells with retrovirus vectors obtained using culture media A, group F, group G, etc.

Measurement results of fluorescence intensity are shown in FIG. 4.

The virus supernatant obtained on each day by the culture method of Example 2-2 was evaluated for the fluorescence intensity, and the average value of the virus supernatants obtained over 4 days was calculated. As shown in FIG. 4, the fluorescence intensities of the retrovirus supernatants collected using the culture medium groups F and G were about 2 times higher than in the case of using the culture medium A. In other words, when the culture medium groups F and G were used, viruses with higher titer were obtained and the gene was transduced with higher efficiency by the viruses, thereby the fluorescent reporter protein (ZsGreen) was more highly expressed, as compared with the case of using the culture medium A. The use of the culture medium groups F and G also produced a higher fluorescence intensity as compared with the case of using the culture medium H or E.

Example 5

Preparation of VPA-supplemented Culture Medium

To the culture medium A as described in Example 1 were added retinoic acid (ATRA) at a final concentration of 10 nM, and valproic acid (VPA) (manufactured by Wako Pure Chemical Industries, Ltd.) at final concentrations of 500 μM, 1 mM and 2 mM to prepare culture media I-1, I-2 and I-3 respectively (hereinafter, referred to as a culture medium group I). Furthermore, as a comparative control, VPA was added at final concentrations of 500 μM, 1 mM and 2 mM to the culture medium A to prepare culture media J-1, J-2 and J-3 respectively (hereinafter, referred to as a culture medium group J). In addition, a culture medium H which was the culture medium A supplemented with only NaB (final concentration: 5 mM), and a culture medium F-1 which was the culture medium A supplemented with NaB (final concentration: 5 mM) and ATRA (final concentration: 10 nM) were prepared. The composition of each culture medium is shown in Table 3.

TABLE 3

| Culture medium | | ATRA | VPA | NaB |
|---|---|---|---|---|
| A | | — | — | — |
| I-1 | Group I | 10 nM | 500 μM | — |
| I-2 | | 10 nM | 1 mM | — |
| I-3 | | 10 nM | 2 mM | — |
| J-1 | Group J | — | 500 μM | — |
| J-2 | | — | 1 mM | — |
| J-3 | | — | 2 mM | — |
| H | | — | — | 5 mM |
| F-1 | | 10 nM | — | 5 mM |

Example 6

Culture of Retrovirus Producer Cell

The retrovirus producer cell as described in Example 2 was used to prepare virus supernatants. In this Example, the virus supernatants were obtained in the same manner as Example 2-1 except that the culture media A, group I, group J, H and F-1 as described in Example 5 were used. However, virus supernatants collected over 3 days were mixed and evaluated in this Example, whereas virus supernatants were collected over 4 days in Example 2-1. Gene transduction was carried out in the same manner as Example 2-2 except that the virus supernatants were diluted 10-fold. Evaluation of gene transduction efficiency was carried out in the same manner as Example 2-3.

Figure 5:
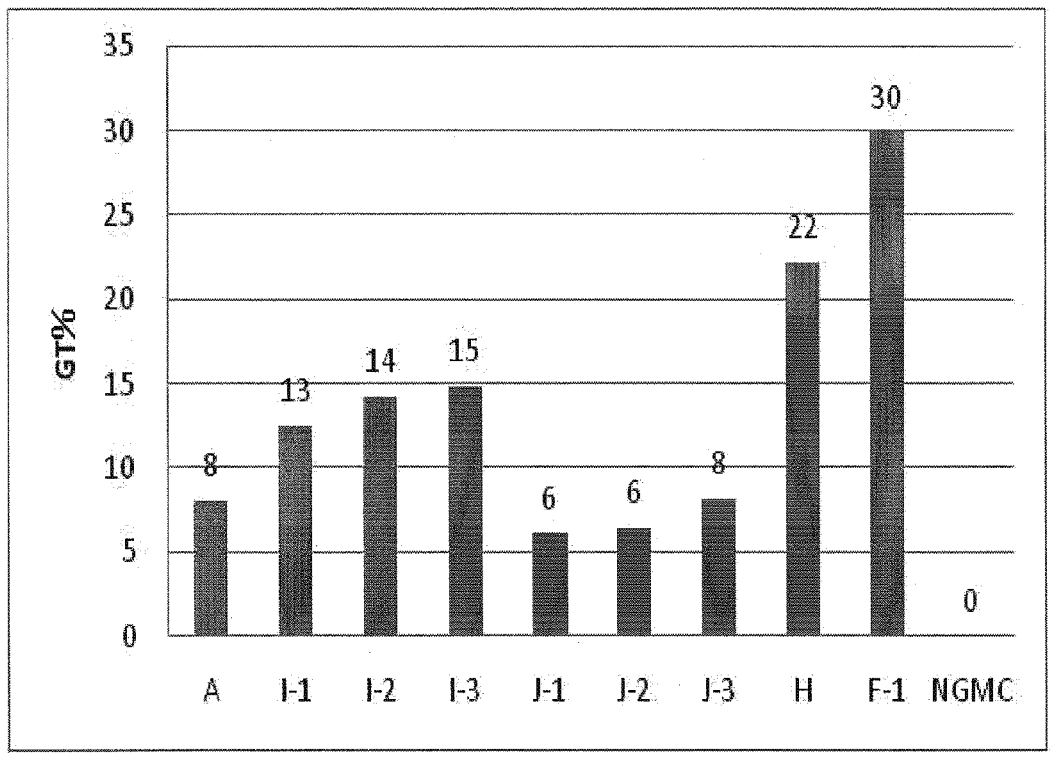
FIG. 5 shows gene transduction efficiency of SUP-T1 cells with retrovirus vectors obtained using culture media A, group I, group J, etc.

Measurement results of gene transduction efficiency are shown in FIG. 5.

As shown in FIG. 5, the gene transduction efficiencies of the retrovirus supernatants collected using the culture medium group I were about 2 times higher than in the case of using the culture medium A. In other words, when the culture medium group I was used, viruses with higher titer were obtained and the ZsGreen gene was transduced with higher efficiency by the viruses as compared with the case of using the culture medium A. The use of the culture medium group I also produced higher effects as compared with the case of using the culture medium group J (addition of only VPA). In addition, the use of the culture medium F-1 produced a higher effect as compared with the case of using the culture medium H (addition of only NaB), which was the same as the result of Example 4 shown in FIG. 2.

Example 7

1. Culture of Retrovirus Producer Cell

A HEK 293 T cell (ATCC CRL-11268) was transfected with the codon modified TCR and siRNA-coexpression retroviral vector (MS-MA24-siTCR) described in WO 2008/153029 using Retrovirus Packaging Kit Eco (manufactured by TAKARA BIO INC.) according to the manufacturer's protocol to obtain an ecotropic retrovirus supernatant. The virus supernatant was filtered with a 0.45 μm filter (Milex HV, manufactured by Millipore). A PG13 cell was infected with the filtrate by a method using polybrene, and then cloned by a limiting dilution method.

2. Pilot Scale Culture of Retrovirus Producer Cell

A working cell bank (WCB) prepared from the cloned cell obtained in Example 7-1 was thawed in a water bath at 37° C. The cell solution thus thawed was put into a 15 mL centrifuging tube. After addition of a complete medium [a DMEM medium (manufactured by Gibco) containing 10% fetal bovine serum (10% FBS, manufactured by SAFC Biosciences)], the tube was subjected to centrifugation (500×g, 5 minutes, 20° C.). After the centrifugation, a supernatant was removed, and the cells were suspended in 10 mL of the complete medium and then counted. After cell counting, the cell suspension was adjusted with the complete medium to $78.5 \times 10^4$ cells/mL. To a 100 mm dish for cell culture (manufactured by IWAKI) were added 1 mL of the cell suspension and 14.7 mL of the complete medium. The cell culture was carried out in a $CO_2$ incubator (37° C., 95% of humidity, 5% $CO_2$). The cell was subcultured at intervals of 3 days. At the 1st passage, the cell suspension was seeded at the cell density of $1 \times 10^4$ cells/cm$^2$ and the volume of 0.2 mL/cm$^2$. At the 2nd passage, 45.0 mL/flask of the cell suspension was seeded at the cell density of $1.0 \times 10^4$ cells/cm$^2$ and the volume of 0.2 mL/cm$^2$ into CELLBIND-treated T225 flasks for cell culture (manufactured by CORNING). Three days after the start of culture at the 2nd passage, a culture supernatant was removed and replaced with the culture medium H, F-1, K, L or B-1 as shown in Table 4 (volume: 0.1 mL/cm$^2$). Herein, dexamethasone (DEX) (manufactured by Nacalai tesque) was added to the culture media K and L at a final concentration of 100 nM. On the day immediately following the culture medium replacement, the culture medium was collected and replaced with a fresh culture medium that was of the same kind as that of the collected culture medium. After lapse of 3 days at the 2nd passage, the cell culture was carried out at 32° C., 95% of humidity and 5% $CO_2$. The collection and replacement of the culture medium were carried out a total of 3 times for consecutive 3 days, provided that for the 3rd time, only the collection of the culture medium was carried out and a fresh culture medium thereof was not added. The collected culture supernatants (the 1st, 2nd, and 3rd times) were mixed and then filtered through a filter with pore size of 0.22 μm (manufactured by Millipore). The filtrate was aliquoted and then kept at −80° C. as a retrovirus supernatant.

TABLE 4

| Culture medium | ATRA | NaB | TSA | DEX |
| --- | --- | --- | --- | --- |
| H | — | 5 mM | — | — |
| F-1 | 10 nM | 5 mM | — | — |
| K | — | 5 mM | — | 100 nM |
| L | 10 nM | 5 mM | — | 100 nM |
| B-1 | 10 nM | — | 500 nM | — |

3. Evaluation of Gene Transduction with Retrovirus Supernatant

The gene transduction efficiencies of the retrovirus supernatants were determined.

RetroNectin and an anti-CD3 antibody (OKT3, Janssen Pharmaceutical Companies) were dissolved in PBS at 25 μg/mL and 5 μg/mL respectively. This solution was added to a tissue culture treated 6-well plate in an amount of 1 mL/well, and allowed to stand at 37° C. for 5 hours. Then, the solution was removed, and each well was washed twice with 1 mL of GT-T-RetroIII (manufactured by TAKARA BIO INC., hereinafter referred to as RetroIII). Then, each well was washed with 1 mL of a culture medium prepared by supplementing RetroIII with IL-2 (manufactured by NOVARTIS) at a final concentration of 600 IU/mL, Fungizone (manufactured by Bristol-Myers Squibb) a final concentration of 0.5 μg/mL and autologous plasma at 0.6% (hereinafter, referred to as CM), to prepare a RetroNectin/anti-CD3 antibody immobilized plate.

A peripheral blood mononuclear cell (PBMC) separated from human peripheral blood was suspended at $0.2 \times 10^6$ cells/mL in CM. To the RetroNectin/anti-CD3 antibody immobilized plate was added 6.7 mL of the cell suspension at 0.7 mL/cm$^2$, and culture was started ($0.14 \times 10^6$ mL/cm$^2$).

On the 4th day of culture, gene transduction was carried out as follows. For each of the retrovirus supernatants collected using the culture media H, F-1, K, L and B-1, an undiluted solution and a 5-fold diluted solution were prepared. For the dilution of the retrovirus supernatants, ACD-A, the 5% albumin solution and the 2% albumin solution were used. As a vessel for gene transduction, a 24-well nontreated plate was used. The 24-well nontreated plate was treated at 4° C. overnight with addition of 0.5 mL/well of a solution of RetroNectin (registered trademark, manufactured by TAKARA BIO INC.) which was previously diluted with ACD-A so as to have the final concentration of 20 μg/mL. After the solution of RetroNectin was removed from the plate, the plate was washed twice with 0.5 mL/well of ACD-A. To each well of the plate was added 1 mL of each virus diluted solution.

The plate was subjected to centrifugation (32° C., 2000×g, 2 hours). After centrifugation, a supernatant of the virus diluted solution was removed from each well. Each well was washed 3 times with 0.5 mL of the 1.5% albumin solution. The cultured cell suspension was collected, and suspended in CM at $0.145 \times 10^6$ cells/mL. To each well of the washed 24-well nontreated plate as described above was added 1 mL of the cell suspension ($0.0725 \times 10^6$ cells/cm$^2$). The plate was subjected to centrifugation (32° C., 1000×g, 10 minutes). After centrifugation, the cell was cultured for 4 hours in a $CO_2$ incubator (37° C., 95% of humidity, 5% $CO_2$). Then, the cell suspension was diluted 5-fold with CM and added to a tissue culture treated 6-well plate, and the cell culture was continued. On the 7th day of culture, the cell suspension was diluted 2-fold with an equal amount of CM, and the cell culture was further continued.

On the 10th day of culture, in order to check the gene transduction efficiency of the retrovirus, the cells were stained with MAGE-A4 tetramer-PE (manufactured by Ludwig) and Human CD8-APC-Cy7 (manufactured by Becton Dickinson), and subjected to a flow cytometer to determine the percentage of the cells that were CD8-positive and tetramer-positive. Specifically, $0.3 \times 10^6$ cells of the infected and cultured cell were put into an Eppendorf tube, and then precipitated by centrifugation (4° C., 500×g, 5 minutes). After a supernatant was removed, the precipitated cells were suspended in 950 μL of 0.5% BSA/PBS. Then, the cells were precipitated again by centrifugation (4° C., 500×g, 5 minutes). After a supernatant was removed, the precipitated cells were suspended in a mixture of 1 μL of MAGE-A4 tetramer-PE and 8 μL of 0.5% BSA, and reacted at 4° C. for 30 minutes. Then, 1 μl of Human CD8-APC-Cy7 was added to the cell suspension, and reacted at 4° C. for 30 minutes. After the reaction, 950 μL of 0.5% BSA/PBS was added to the cell suspension. After removal of a supernatant by centrifugation (4° C., 500×g, 5 minutes) was carried out 2 times, the cells were suspended in 400 μl of 0.5% BSA/PBS. The cell suspension was subjected to flow cytometry measurement.

4. Flow Cytometry Analysis

Flow cytometry analyses were carried out using a BD FACSCanto II flow cytometer according to the instructions attached to the equipment. The percentage of tetramer-positive cells present in CD8-positive cells was determined as follows. On a 2-parameter histogram of APC-Cy7 and PE-detected parameters (x-axis: fluorescence intensity of APC-Cy7, y-axis: fluorescence intensity of PE), a region displaying the fluorescence intensities of cells not expressing APC-Cy7 (CD8) and PE (MAGE-A4 tetramer) was checked by using an isotype control. While boundaries were defined around the region, the histogram was divided into 4 quadrants. A quadrant region displaying the fluorescence intensities of cells expressing APC-Cy7 and PE was determined, and the percentage (%) of the cell number in the quadrant region was measured. After the measurement, a gene transduction efficiency (GT %) was determined by the following equation.

Figure 6:
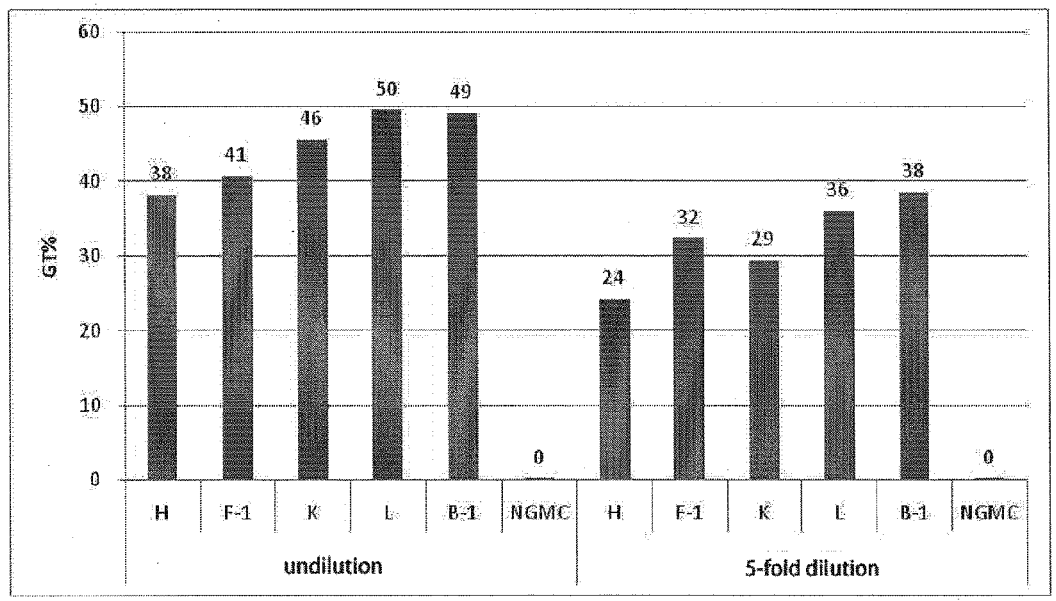
FIG. 6 shows gene transduction efficiency in PBMC with retrovirus vectors obtained using culture media H, F-1, K, L, and B-1.

GT %=the number of CD8 and tetramer-positive cells/ the number of CD8-positive cells Measurement results of gene transduction efficiency are shown in FIG. 6. As shown in FIG. 6, the gene transduction efficiencies of the retrovirus supernatants collected using the culture media F-1, K, L and B-1 were remarkably higher than in the case of using the culture medium H which was the basal medium A supplemented with NaB. In other words, viruses with high titer were obtained and transduction of the desired gene was attained with high efficiency, when the method of the present invention was applied not only to a fluorescent protein-expressing virus vector as described in Examples 2 and 4, but also to other virus vectors, and when the method of the present invention was conducted at a pilot scale larger than an experimental scale.

5. Evaluation of RNA Copy Number in Retrovirus Supernatant

The RNA copy number in the retrovirus supernatant was measured.

Figure 7:
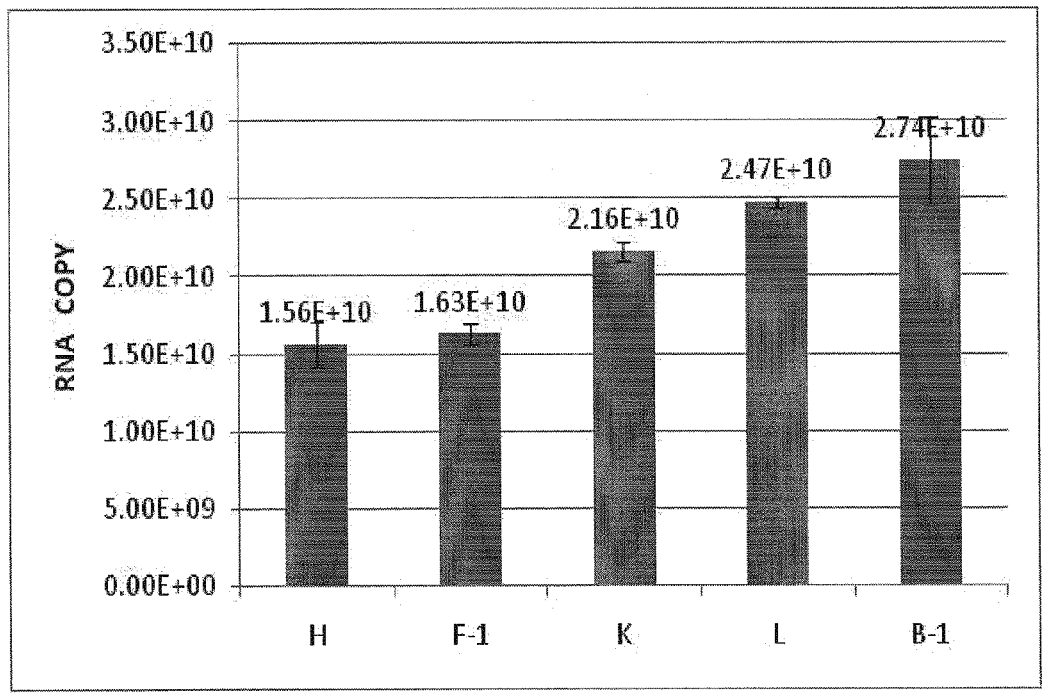
FIG. 7 shows RNA copy numbers of retrovirus vectors obtained using media H, F-1, K, L, and B-1.

The RNA copy number was determined using Retrovirus Titer Set (for Real Time PCR) (manufactured by TAKARA BIO INC.) according to a standard method described in the directions for use attached to the product. As shown in FIG. 7, the measurement results showed that the RNA copy number (in Figures, referred to as RNA COPY) was remarkably increased by a combination of NaB with either or both of ATRA and DEX, as compared with the case of using the culture medium H which was the basal medium A supplemented with NaB, in the same way as the gene transduction efficiency results of Example 7-4.

Example 8

Preparation 2 of TSA-supplemented Culture Medium

To the culture medium A were added dexamethasone (DEX) at a final concentration of 100 nM, retinoic acid (ATRA) at a final concentration of 1 μM, and trichostatin A (TSA) at final concentrations of 50 nM and 500 nM to prepare culture media M-1 and M-2 respectively (hereinafter, referred to as a culture medium group M). In addition, culture media D-1 and D-2 (hereinafter, referred to as a culture medium group D) which were the culture medium A supplemented with TSA at final concentrations 50 nM and 500 nM respectively, a culture medium H which was the culture medium A supplemented with only NaB (final concentration: 5 mM), and a culture medium N which was the culture medium A supplemented with NaB (final concentration: 5 mM), retinoic acid (ATRA) at a final concentration of 100 nM and dexamethasone (DEX) at a final concentration of 100 nM were prepared. The composition of each culture medium is shown in Table 5.

TABLE 5

| Culture medium | | ATRA | NaB | TSA | DEX |
|---|---|---|---|---|---|
| M-1 | Group M | 1 μM | — | 50 nM | 100 nM |
| M-2 | | 1 μM | — | 500 nM | 100 nM |
| D-1 | Group D | — | — | 50 nM | — |
| D-2 | | — | — | 500 nM | — |
| H | | — | 5 mM | — | — |
| N | | 100 nM | 5 mM | — | 100 nM |

Example 9

1. Culture of Retrovirus Producer Cell

The retrovirus producer cell as described in Example 7-1 was used to prepare virus supernatants. In this Example, the virus supernatants were obtained in the same manner as Example 2-1 except that the culture media as described in Example 8 were used. However, virus supernatants collected over 3 days were mixed and evaluated in this Example, whereas virus supernatants were collected over 4 days in Example 2-1.

2. Evaluation of Gene Transduction with Retrovirus Supernatant

Gene transduction was carried out in the same manner as Example 7-3 except that Human CD8-FITC (manufactured by Becton Dickinson) was used as a CD8 antibody. Evaluation of gene transduction efficiency was carried out in the same manner as Example 7-4.

Figure 8:
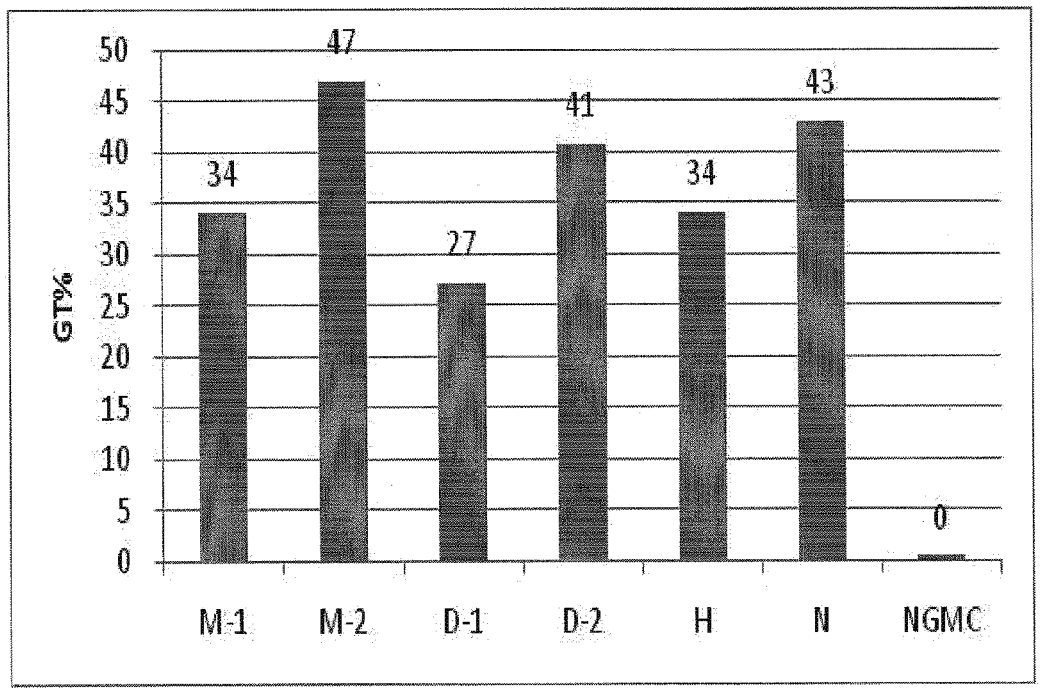
FIG. 8 shows gene transduction efficiency in PBMC with retrovirus vectors obtained using culture media group M, group D, H, and N.

Measurement results of gene transduction efficiency are shown in FIG. 8. As shown in FIG. 8, in comparisons between M-1 and D-1, M-2 and D-2, and H and N, the gene transduction efficiencies of the retrovirus supernatants collected using the culture media containing a combination of ATRA, DEX, and either NaB or TSA were remarkably higher than in the cases of using the culture medium group D and the culture medium H which were the culture medium A supplemented with only NaB or TSA. Regarding TSA, the concentration of 500 nM was more effective than 50 nM.

3. Evaluation of RNA Copy Number in Retrovirus Supernatant

The RNA copy number in the retrovirus supernatant was measured.

Figure 9:
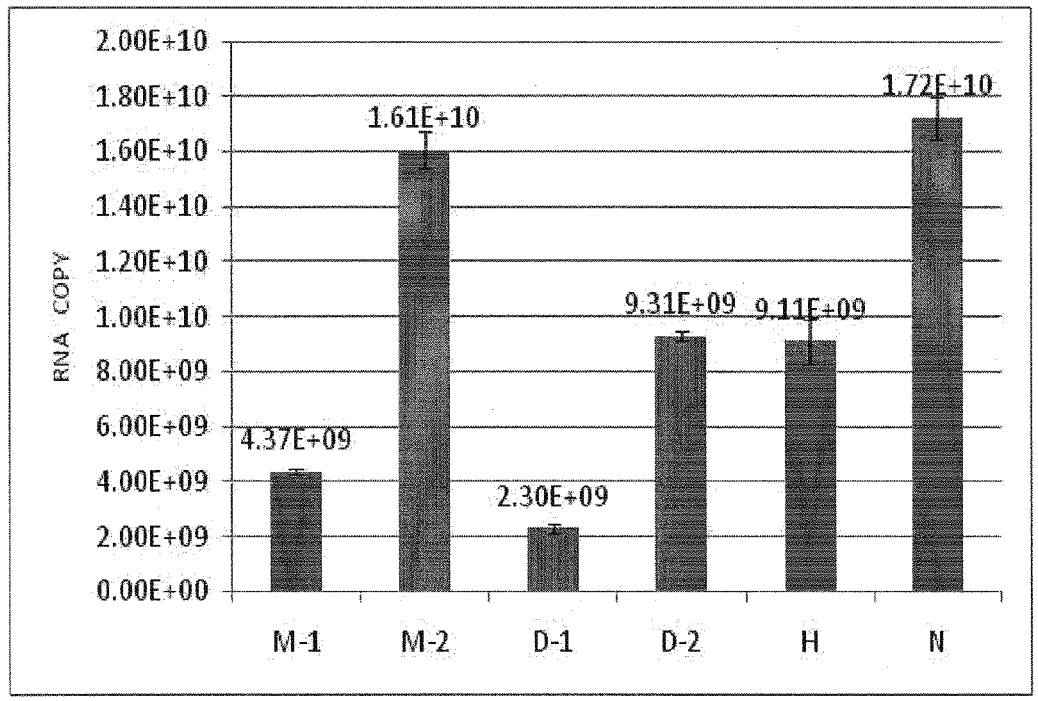
FIG. 9 shows RNA copy numbers of retrovirus vectors obtained using culture media group M, group D, H, and N.

The RNA copy number was determined using Retrovirus Titer Set (for Real Time PCR) (manufactured by TAKARA BIO INC.) according to a standard method described in the directions for use attached to the product. As shown in FIG. 9, the measurement results showed that in comparisons between M-1 and D-1, M-2 and D-2, and H and N, the RNA copy number was remarkably increased by a combination of both of ATRA and DEX with either NaB or TSA, as compared with the cases of using the culture media which were supplemented with only NaB or TSA, in the same way as the gene transduction efficiency results of Example 9-2. Regarding TSA, the concentration of 500 nM was more effective than 50 nM.

Example 10

Preparation 3 of TSA-supplemented Culture Medium

Culture media were prepared so as to be the final concentrations shown in Table 6, in the same manner as Example 1.

TABLE 6

| Culture medium | | ATRA | TSA | NaB |
|---|---|---|---|---|
| A | | — | — | — |
| O-1 | Group O | 10 nM | 500 μM | — |
| O-2 | | 100 nM | 500 μM | — |
| D | | — | 500 μM | — |
| E-1 | Group E | 10 nM | — | — |
| E-2 | | 100 nM | — | — |
| H | | — | — | 5 mM |
| F-1 | | 10 nM | — | 5 mM |

Example 11

Culture of Retrovirus Producer Cell

The retrovirus producer cell as described in Example 2 was used to prepare virus supernatants. The virus supernatants were obtained in the same manner as Example 2-1 except that the culture media as described in Example 10 were used. However, in this Example, virus supernatants collected over 4 days were mixed and evaluated and virus supernatants collected over 3 days were mixed and evaluated. Gene transduction was carried out in the same manner as Example 2-2 except that the virus supernatants were diluted 10-fold. Evaluation of gene transduction efficiency and fluorescence intensity was carried out in the same manner as Example 2-3.

Figure 10:
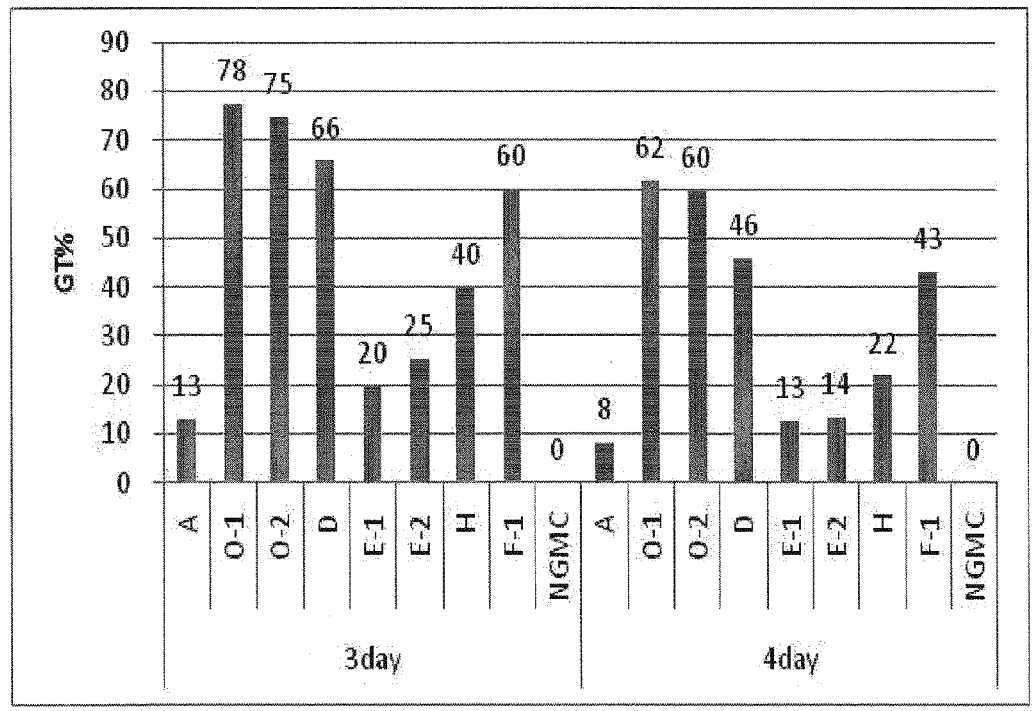
FIG. 10 shows gene transduction efficiency in SUP-T1 cells with retrovirus vectors obtained using culture media A, group O, D, group E, H, and F-1.

Measurement results of gene transduction efficiency are shown in FIG. 10.

As shown in FIG. 10, the gene transduction efficiencies of the retrovirus supernatants collected using the culture medium group O were about 6 to 8 times higher than in the case of using the culture medium A. The retrovirus supernatants collected over 4 days had greater effect of increasing the gene transduction efficiency from that of a group of controls than the retrovirus supernatants collected over 3 days.

Figure 11:
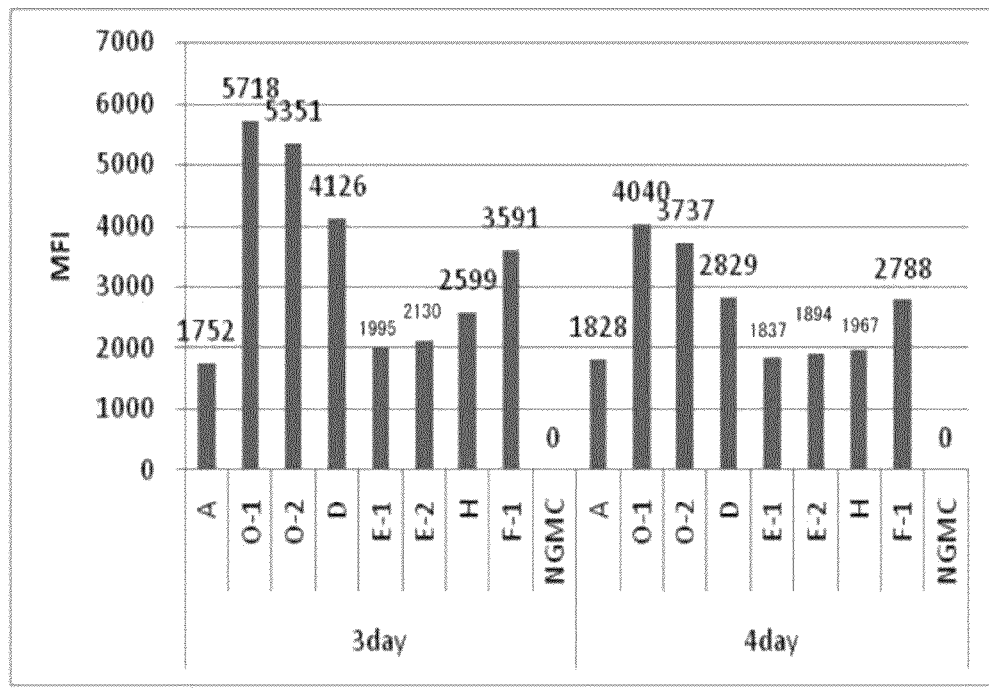
FIG. 11 shows expression intensity of a gene that has been transduced into SUP-T1 cells with retrovirus vectors obtained using culture media A, group O, D, group E, H, and F-1.

Measurement results of fluorescence intensity are shown in FIG. 11.

As shown in FIG. 11, the fluorescence intensities of the retrovirus supernatants collected using the culture medium group O were about 2 to 3.5 times higher than in the case of using the culture medium A.

Example 12

Preparation of 9-cis Retinoic Acid (9-cis) (Manufactured by Nacalai Tesque) or AM80-supplemented Culture Medium Culture media were prepared so as to be the final concentrations shown in Table 7, in the same manner as Example 1. Tamibarotene (manufactured by Sigma) was used as AM80.

TABLE 7

| Culture medium | | ATRA | 9-cis | AM80 | NaB |
|---|---|---|---|---|---|
| A | | — | — | — | — |
| P-1 | Group P | — | 10 nM | — | 5 mM |
| P-2 | | — | 100 nM | — | 5 mM |
| P-3 | | — | 1 μM | — | 5 mM |
| Q-1 | Group Q | — | 10 nM | — | — |
| Q-2 | | — | 100 nM | — | — |
| Q-3 | | — | 1 μM | — | — |
| R-1 | Group R | — | — | 10 nM | 5 mM |
| R-2 | | — | — | 100 nM | 5 mM |
| R-3 | | — | — | 1 μM | 5 mM |
| S-1 | Group S | — | — | 10 nM | — |
| S-2 | | — | — | 100 nM | — |
| S-3 | | — | — | 1 μM | — |
| E | | 10 nM | — | — | — |
| H | | — | — | — | 5 mM |
| F-1 | | 10 nM | — | — | 5 mM |

Example 13

Culture of Retrovirus Producer Cell

The retrovirus producer cell as described in Example 2 was used to prepare virus supernatants. The virus supernatants were obtained in the same manner as Example 2-1 except that the culture media as described in Example 12 were used. However, virus supernatants collected over 3 days were mixed and evaluated in this Example, whereas virus supernatants were collected over 4 days in Example 2-1. Gene transduction was carried out in the same manner as Example 2-2 except that the virus supernatants were diluted 10-fold. Evaluation of gene transduction efficiency was carried out in the same manner as Example 2-3.

Figure 12:
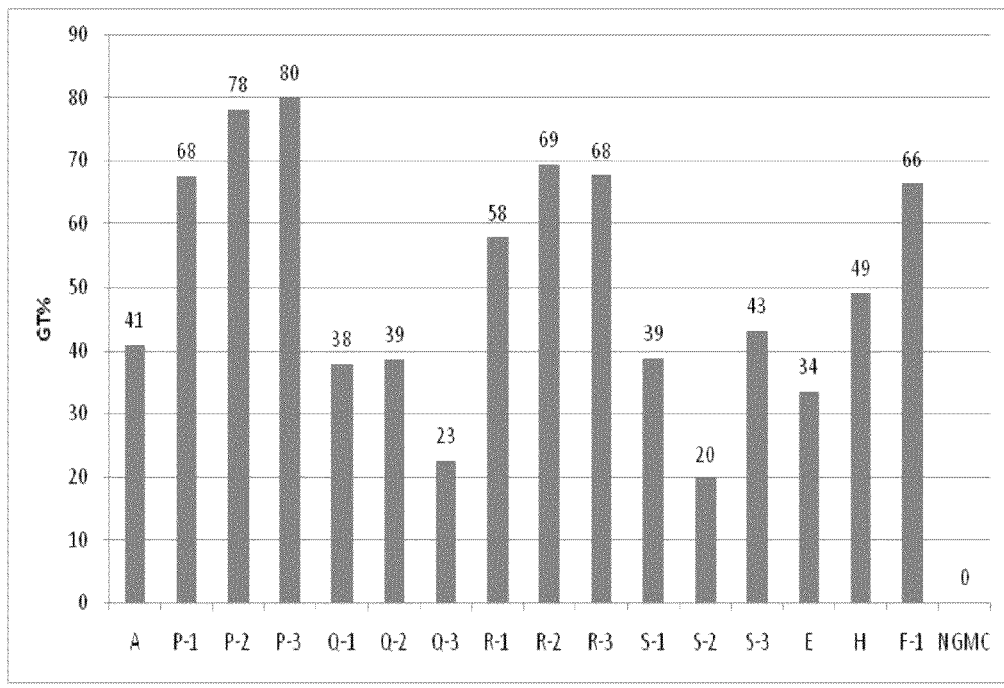
FIG. 12 shows gene transduction efficiency in SUP-T1 cells with retrovirus vectors obtained using culture media A, group P, group Q, group R, group S, E, H, and F-1.

Measurement results of gene transduction efficiency are shown in FIG. 12.

As shown in FIG. 12, the gene transduction efficiencies of the retrovirus supernatants collected using the culture medium groups P and R were about 1.5 to 2 times higher than in the case of using the culture medium A. The gene transduction efficiencies of the retrovirus supernatants collected using the culture medium groups Q and S wherein only 9-cis or AM80 were added were about the same as or lower than in the case of using the culture medium A.

Example 14

Preparation of Suberoylanilide Hydroxamic Acid (SAHA) (Manufactured by CAYMAN)-supplemented Culture Medium Culture media were prepared so as to be the final concentrations shown in Table 8, in the same manner as Example 1.

TABLE 8

| Culture medium | | ATRA | SAHA | NaB |
|---|---|---|---|---|
| A | | — | — | — |
| T-1 | Group T | 100 nM | 1 μM | — |
| T-2 | | 100 nM | 5 μM | — |
| T-3 | | 100 nM | 10 μM | — |
| T-4 | | 100 nM | 25 μM | — |
| U-1 | Group U | — | 1 μM | — |
| U-2 | | — | 2.5 μM | — |
| U-3 | | — | 5 μM | — |
| U-4 | | — | 7.5 μM | — |
| U-5 | | — | 10 μM | — |
| U-6 | | — | 15 μM | — |
| U-7 | | — | 20 μM | — |
| U-8 | | — | 25 μM | — |
| U-9 | | — | 30 μM | — |
| U-10 | | — | 40 μM | — |
| U-11 | | — | 50 μM | — |
| E-2 | | 100 nM | — | — |
| H | | — | — | 5 mM |

Example 15

Culture of Retrovirus Producer Cell

The retrovirus producer cell as described in Example 2 was used to prepare virus supernatants. The virus supernatants were obtained in the same manner as Example 2-1 except that the culture media as described in Example 14 were used. However, virus supernatants collected over 3 days were mixed and evaluated in this Example, whereas virus supernatants were collected over 4 days in Example 2-1. Gene transduction was carried out in the same manner as Example 2-2 except that the virus supernatants were diluted 10-fold. Evaluation of gene transduction efficiency was carried out in the same manner as Example 2-3.

Figure 13:
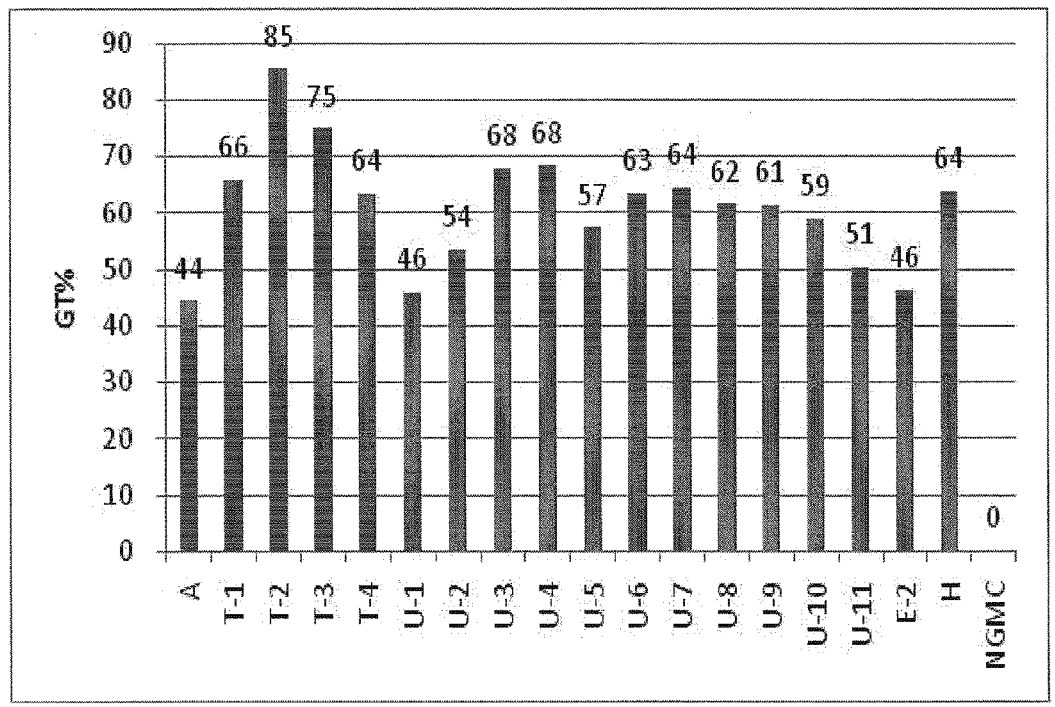
FIG. 13 shows gene transduction efficiency in SUP-T1 cells with retrovirus vectors obtained using culture media A, group T, group U, E-2, and H.

Measurement results of gene transduction efficiency are shown in FIG. 13.

As shown in FIG. 13, the gene transduction efficiencies of the retrovirus supernatants collected using the culture medium group T were about 1.4 to 1.9 times higher than in the case of using the culture medium A. In addition, the gene transduction efficiencies of the retrovirus supernatants collected using the culture medium group T were higher than in the case of using the corresponding culture media of the group U which contained SAHA at the same concentrations.

Example 16

Preparation 2 of NaB-supplemented Culture Medium

To a DMEM which was a medium for cell culture was added inactivated FBS at a volume ratio (V/V) of 1/10 to prepare a basal medium (culture medium V). To the culture medium V was added retinoic acid (ATRA) at a final concentration of 100 nM and sodium butyrate (NaB) at a final concentration of 5 mM to prepare a culture medium W.

In addition, a culture medium X which was the culture medium V supplemented with only NaB (final concentration: 5 mM), and a culture medium Y which was the culture medium V supplemented with only ATRA (final concentration: 100 nM) were prepared. The composition of each culture medium is shown in Table 9.

TABLE 9

| Culture medium | ATRA | NaB |
|---|---|---|
| V | — | — |
| W | 100 nM | 5 mM |
| X | — | 5 mM |
| Y | 100 nM | — |

Example 17

Culture of Retrovirus Producer Cell

The retrovirus producer cell as described in Example 2 was used to prepare virus supernatants. The virus supernatants were obtained in the same manner as Example 2-1 except that the culture media as described in Example 16 were used. However, virus supernatants collected over 3 days were mixed and evaluated in this Example, whereas virus supernatants were collected over 4 days in Example 2-1. Gene transduction was carried out in the same manner as Example 2-2 except that the virus supernatants were diluted 10-fold. Evaluation of gene transduction efficiency and fluorescence intensity was carried out in the same manner as Example 2-3.

Figure 14:
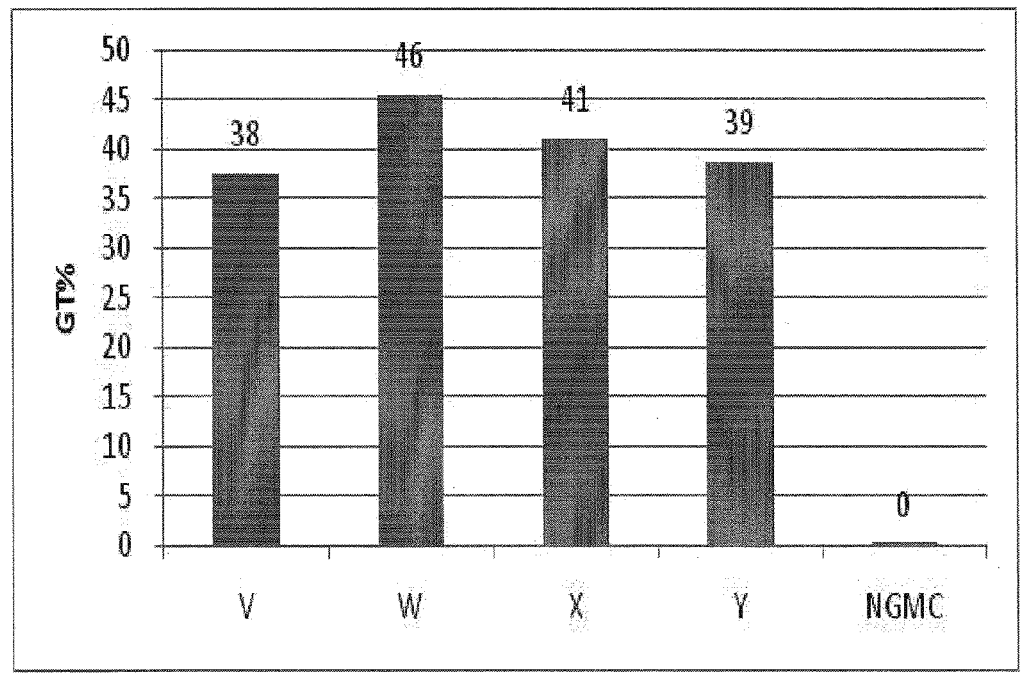
FIG. 14 shows gene transduction efficiency in SUP-T1 cells with retrovirus vectors obtained using culture media V, W, X, and Y.

Measurement results of gene transduction efficiency are shown in FIG. 14.

As shown in FIG. 14, the gene transduction efficiency of the retrovirus supernatant collected using the culture medium W was about 1.2 times higher than in the case of using the culture medium V.

Figure 15:
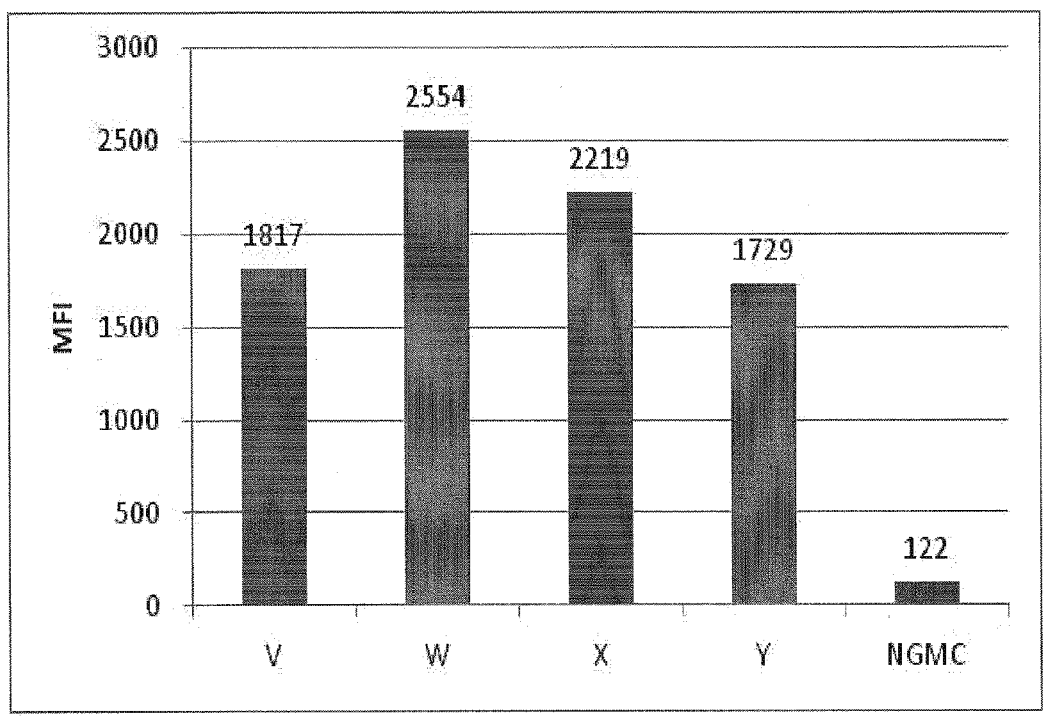
FIG. 15 shows expression intensity of a gene that has been transduced into SUP-T1 cells with retrovirus vectors obtained using culture media V, W, X, and Y.

Measurement results of fluorescence intensity are shown in FIG. 15.

As shown in FIG. 15, the fluorescence intensity of the retrovirus supernatant collected using the culture medium W was about 1.5 times higher than in the case of using the culture medium V.

Industrial Applicability

A virus supernatant with high titer can be easily obtained by using the culture medium of the present invention, and therefore, a virus vector and a high titer composition containing the virus vector can be easily prepared. The virus vector or the above-described composition which is obtained by using the culture medium of the present invention is very useful in the field of gene therapy.

The invention claimed is:

1. A method of producing a retrovirus particle, which comprises a step of culturing a producer cell line which produces the retrovirus particle and producing the retrovirus particle in a culture medium containing retinoic acid and a histone deacetylase inhibitor as active ingredients and a step of harvesting a supernatant containing the retrovirus particle from the culture medium,
    wherein the culture medium contains either 100 nM to 3 μM trichostatin A or 1 mM to 10 mM sodium butyrate as the histone deacetylase inhibitor, and
    wherein the method provides retrovirus particles having higher gene transduction efficiency as compared to culture conditions not comprising retinoic acid and a histone deacetylase inhibitor.

2. The method according to claim 1, wherein the culture medium further contains lipid as an active ingredient.

3. The method according to claim 1, wherein the producer cell line stably produces the retrovirus particle.

4. A method of producing a transformed cell population, which comprises a step of producing a retrovirus vector by the method according to claim 1, and a step of transforming a cell with the retrovirus vector produced in the above step.

5. The method according to claim 3, wherein the producer cell line is prepared by transfecting a nucleic acid encoding a retrovirus vector into packaging cell line PG13.

6. The method according to claim 1, wherein the culture medium contains 5 nM to 200 nM all-trans retinoic acid as the retinoic acid.

7. The method according to claim 1, wherein the culture medium further contains dexamethasone as an active ingredient.

* * * * *